United States Patent
Lee et al.

(10) Patent No.: US 10,869,495 B2
(45) Date of Patent: Dec. 22, 2020

(54) FUNCTIONAL COMPOSITION FOR IMPROVEMENT AND PREVENTION OF ESTROGEN DEFICIENCY IN MENOPAUSAL WOMEN

(71) Applicant: FAMENITY CO., LTD., Gwacheon-si (KR)

(72) Inventors: Ji Won Lee, Gwacheon-si (KR); Sung Su Kim, Gwacheon-si (KR)

(73) Assignee: FAMENITY CO., LTD., Gwacheon-si (KR)

( * ) Notice: Subject to any disclaimer, the term of this patent is extended or adjusted under 35 U.S.C. 154(b) by 514 days.

(21) Appl. No.: 15/748,502

(22) PCT Filed: Oct. 19, 2015

(86) PCT No.: PCT/KR2015/011018
§ 371 (c)(1),
(2) Date: Jan. 29, 2018

(87) PCT Pub. No.: WO2017/069293
PCT Pub. Date: Apr. 27, 2017

(65) Prior Publication Data
US 2018/0199609 A1    Jul. 19, 2018

(51) Int. Cl.
| | |
|---|---|
| A61K 36/00 | (2006.01) |
| A23L 33/105 | (2016.01) |
| A61K 36/53 | (2006.01) |
| A23L 33/10 | (2016.01) |
| A23L 19/00 | (2016.01) |
| B01D 11/02 | (2006.01) |
| A61K 36/28 | (2006.01) |
| A23L 33/00 | (2016.01) |
| A61P 5/30 | (2006.01) |
| A61K 36/286 | (2006.01) |

(52) U.S. Cl.
CPC ............. *A23L 33/105* (2016.08); *A23L 19/00* (2016.08); *A23L 33/10* (2016.08); *A23L 33/40* (2016.08); *A61K 36/28* (2013.01); *A61K 36/286* (2013.01); *A61K 36/53* (2013.01); *A61P 5/30* (2018.01); *B01D 11/02* (2013.01); *A23V 2002/00* (2013.01); *A23V 2200/00* (2013.01); *A23V 2200/30* (2013.01); *A23V 2250/21* (2013.01)

(58) Field of Classification Search
CPC ...................................................... A61K 36/00
USPC ......................................................... 424/725
See application file for complete search history.

(56) References Cited

FOREIGN PATENT DOCUMENTS

KR    1020090062458 A    1/2011

OTHER PUBLICATIONS

International Search Report of PCT/KR2015/011018, dated Jul. 19, 2016, English Translation.
G. Cheng et al.; Isoflavone treatment for acute menopausal symptoms; Menopause; 2007; vol. 14, No. 3, pp. 468/473; The Journal of the North American Menopause Society; Pepper Pike, USA.

*Primary Examiner* — Michael V Meller
(74) *Attorney, Agent, or Firm* — STIP Law Group, LLC

(57) ABSTRACT

The present invention relates to a food composition for improvement and prevention of estrogen deficiency, the composition containing a thistle extract or a thistle and thyme complex extract as an active ingredient. The present invention has advantages of alleviating estrogen deficiency in climacteric women and improving symptoms caused by estrogen deficiency, such as facial flushing, sweating, fatigue, anxiety, depression, memory impairment, insomnia, increased blood cholesterol, weight gain, and reduced bone density.

1 Claim, 7 Drawing Sheets

[FIG. 4]

[FIG. 5]
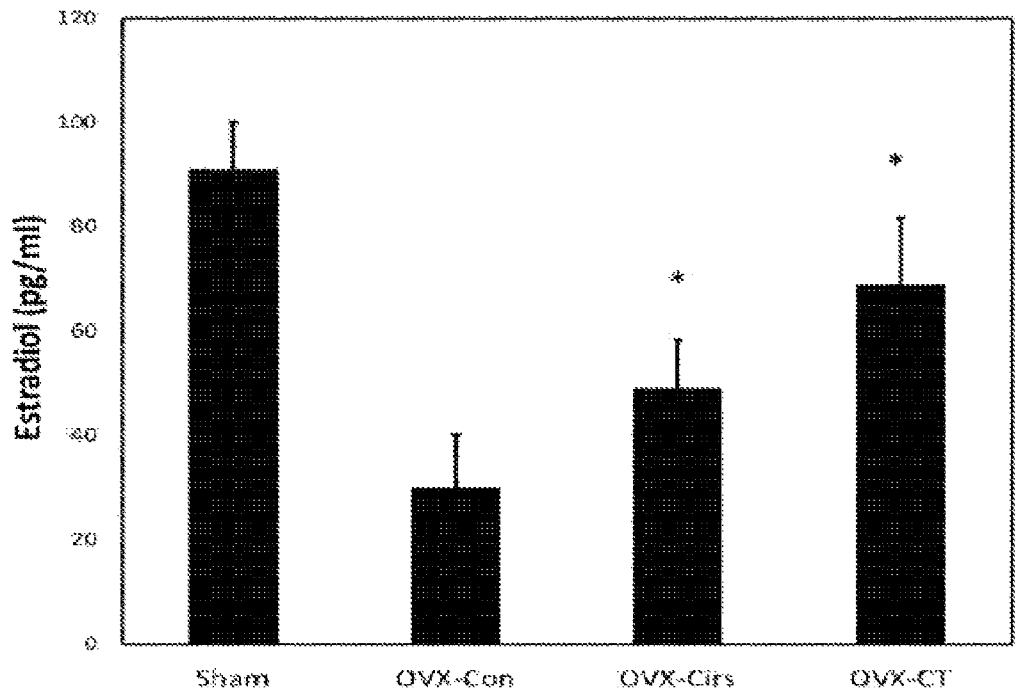
[FIG. 6]
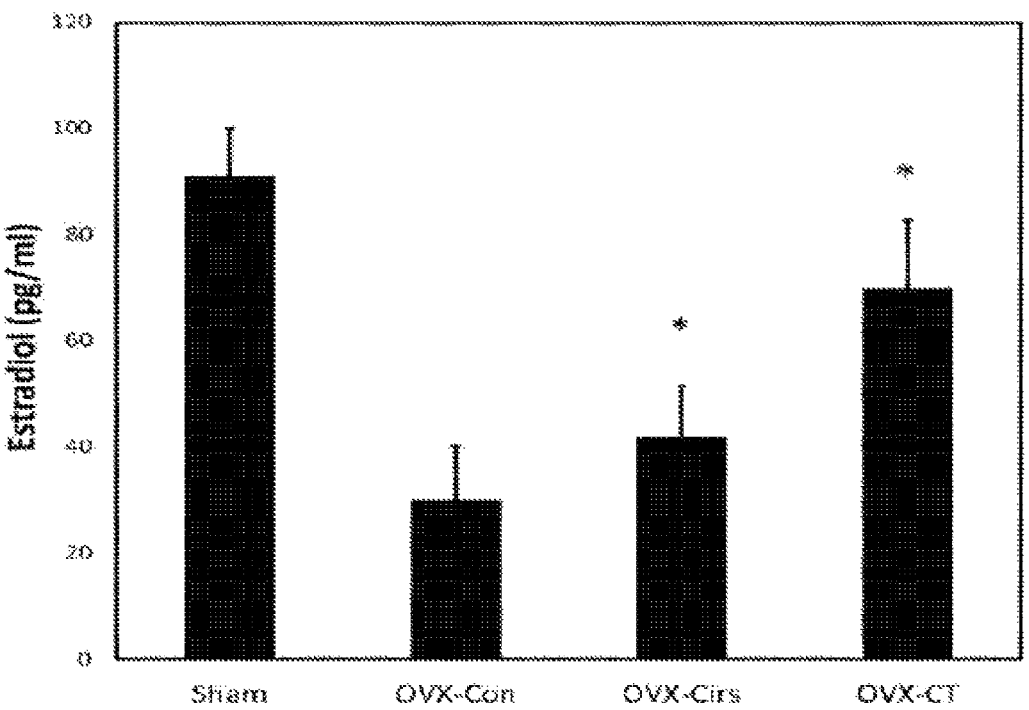

[FIG. 7]
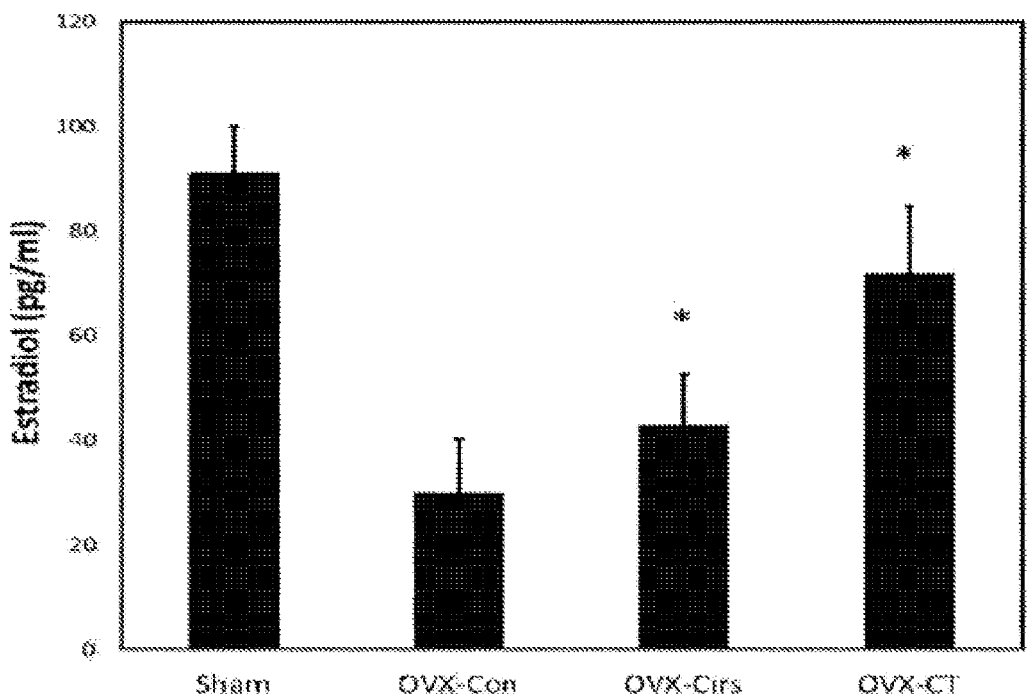
[FIG. 8]
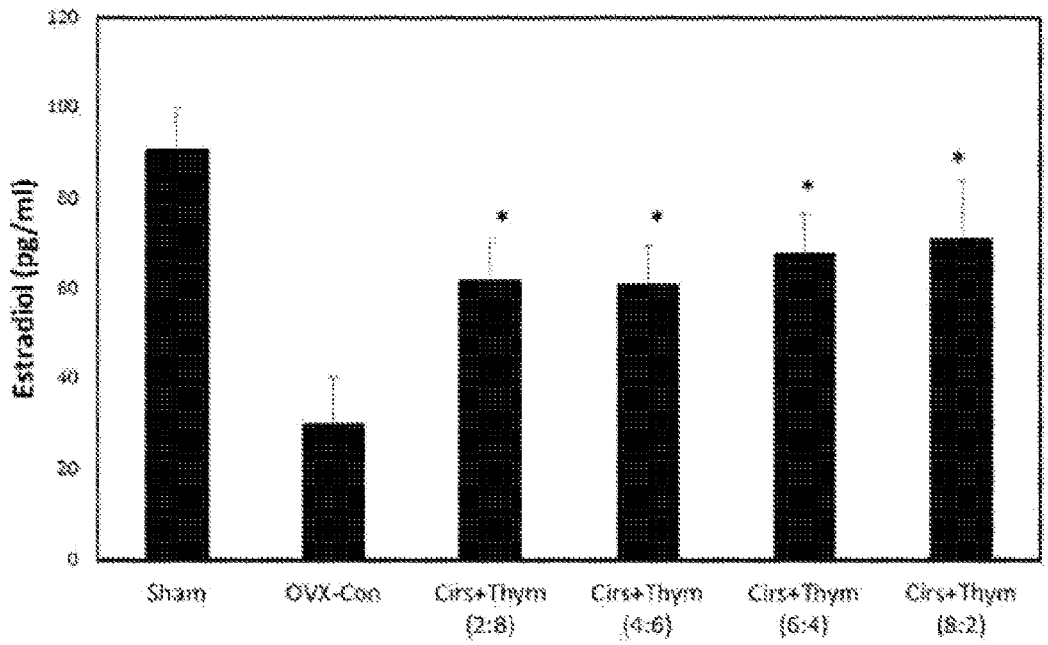

[FIG. 9]
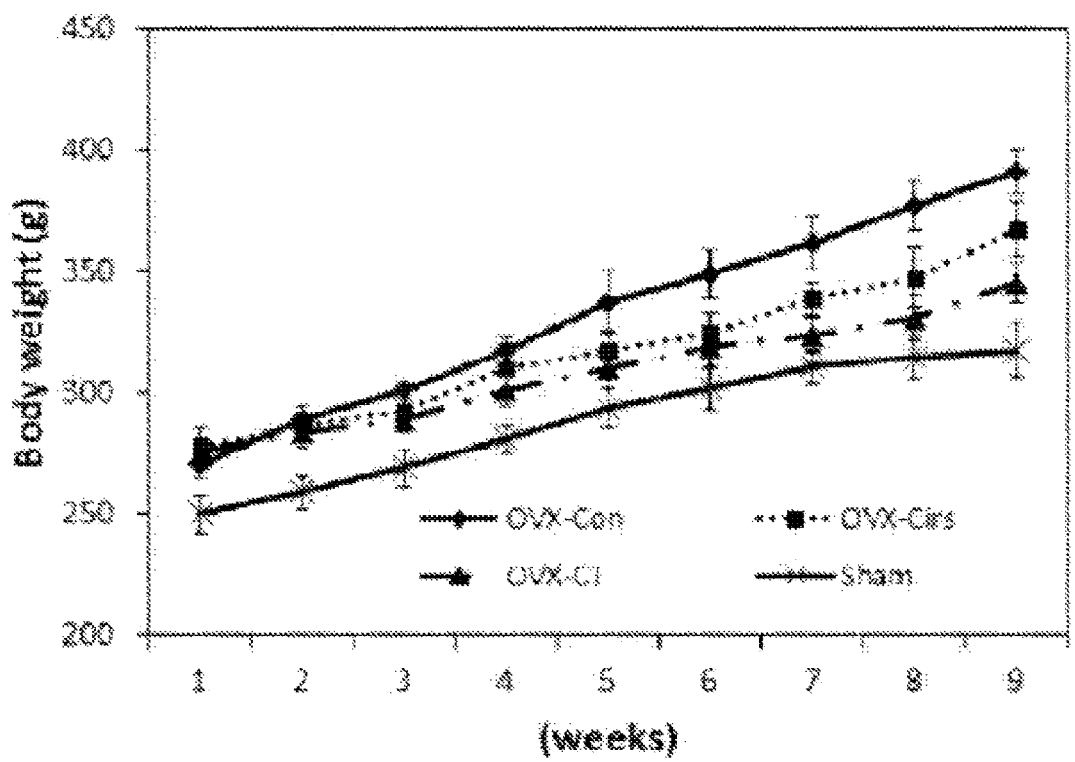
[FIG. 10]
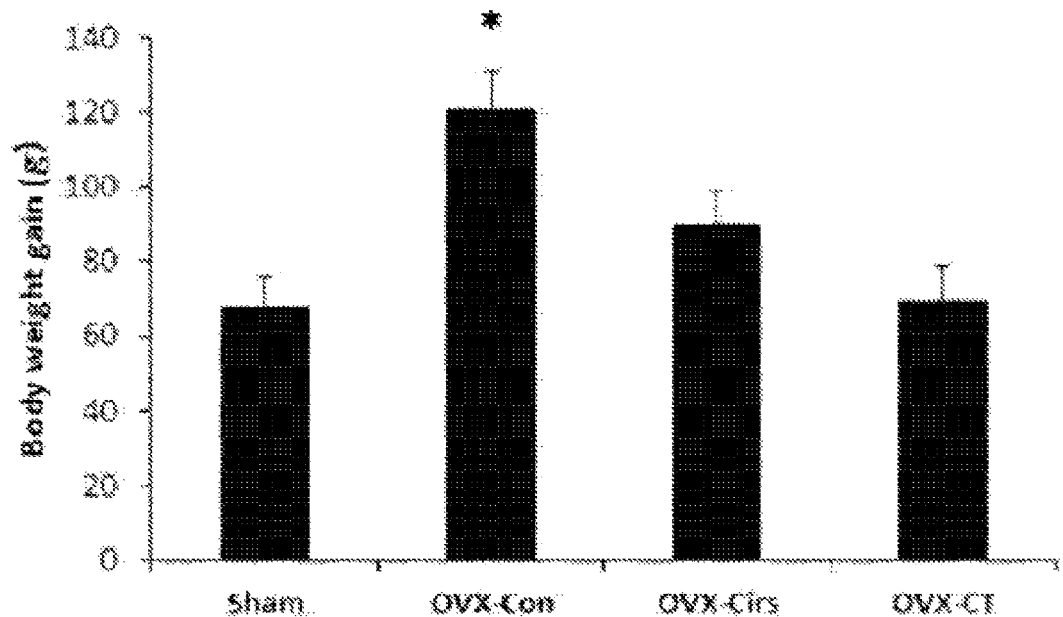

[FIG. 11]
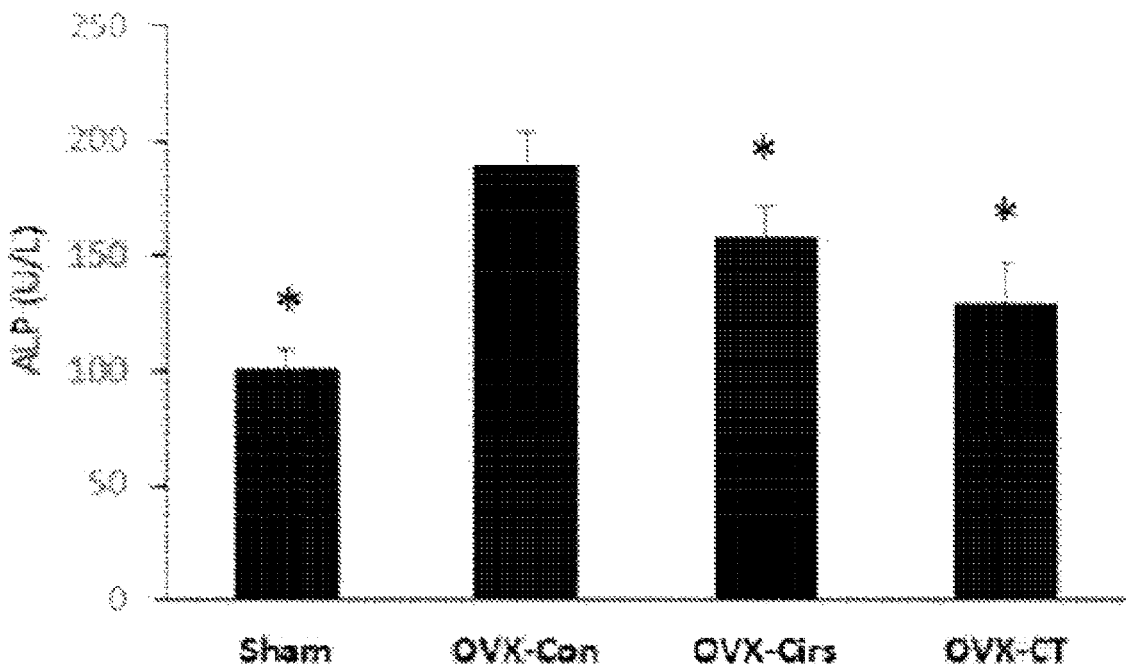
[FIG. 12]
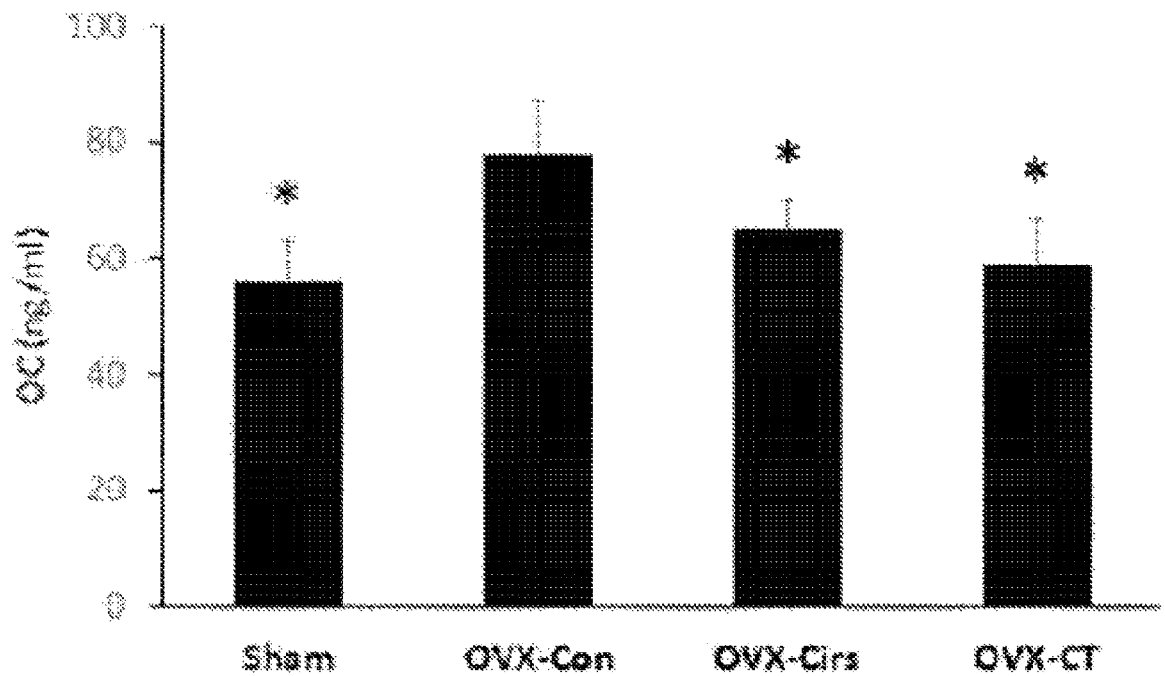

[FIG. 13]
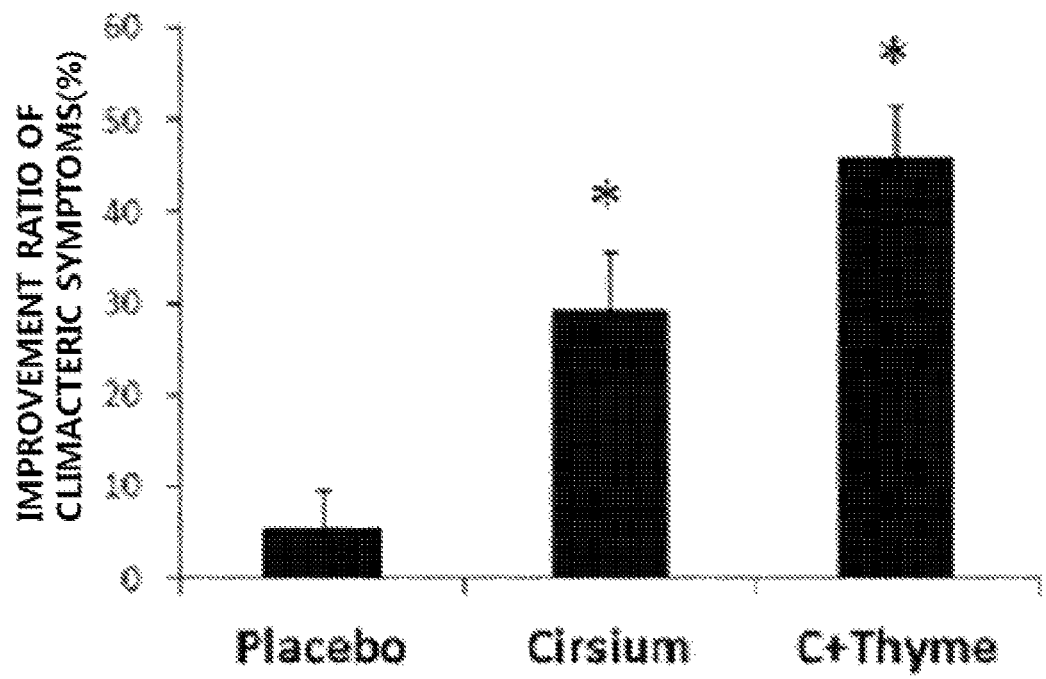
[FIG. 14]
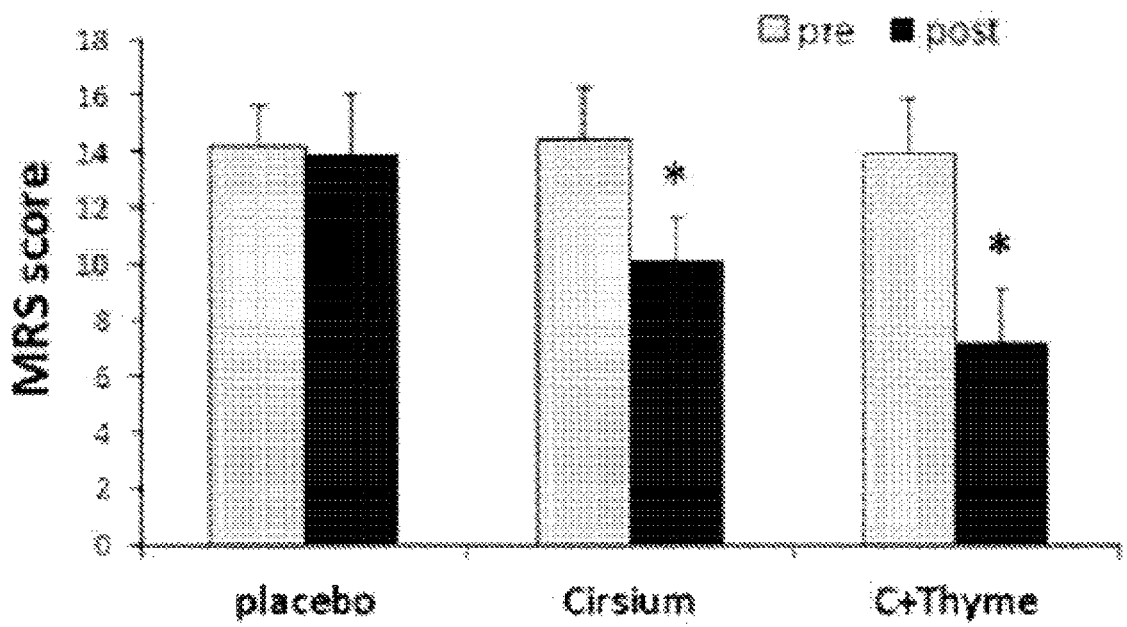

FUNCTIONAL COMPOSITION FOR IMPROVEMENT AND PREVENTION OF ESTROGEN DEFICIENCY IN MENOPAUSAL WOMEN

CROSS-REFERENCE TO RELATED APPLICATIONS

This application is the U.S. National Phase under 35 U.S.C. § 371 of International Application No. PCT/KR2015/011018 filed on Oct. 19, 2015, the disclosures of which are incorporated by reference into the present application.

TECHNICAL FIELD

The present invention relates to a new use of a thistle extract and a thistle and thyme complex extract, and more particularly, to a functional composition for efficiently improving estrogen deficiency according to the women climacteric period by containing a thistle extract as an active ingredient.

BACKGROUND ART

As women age, the function of the ovary deteriorates, and for this reason, the secretion of estrogen significantly decreases. Accordingly, response to follicle stimulating hormone (FSH) and luteinizing hormone (LH) is reduced, and the production of progesterone also decreases. In particular, from the age of mid to late 40's, the probability that the menopause in which the function of the ovary is completely stopped will occur is greatly increased, and the period after the menopause manifests itself commonly refers to the climacteric period, and lasts for 4 to 7 years on average.

When the climacteric period occurs in women, female hormones are no longer produced and as a result, various symptoms occur, such as facial flushing, sweating, fatigue, anxiety, depression, memory impairment, insomnia, increased blood cholesterol, weight gain, and reduced bone density.

In the related art, attempts to use hormonal therapy or phytoestrogen have been made in order to treat the aforementioned female diseases, and for reference, phytoestrogen is a xenoestrogen which is separated from plants without being produced from the endocrine system in vivo, and is known to be contained in most of the plants. Phytoestrogen is structurally similar to estrogen, and thus is known to bind competitively with estrogen to an estrogen receptor in vivo. However, in fact, effects caused by the binding have not been specifically revealed, and it is known that the ratio of binding is also at an insignificant level.

Korean Patent Application No. 10-2009-0062458 discloses a constitution which extracts phytoestrogen by using thistle among various plants. Specifically, Korean Patent Application No. 10-2009-0062458 discloses the contents as follows.

First, in the Korean native thistle, there is a substance which binds to an estrogen receptor. Specifically, in Example 2 of Korean Patent Application No. 10-2009-0062458, it was confirmed that there is a substance which binds to an estrogen receptor in a Korean native thistle extract by using a lac operon of a transformed yeast strain, and that the binding level thereof is comparable to that of quercetin known as a phytoestrogen.

Second, in the Korean native thistle, there is a phytoestrogen. Example 3 of Korean Patent Application No. 10-2009-0062458 confirmed that there is a phytoestrogen by extracting an extract from a root of the Korean native thistle using methanol, and then detecting a phytoestrogen, specifically, genistein, daidzein, or quercetin contained in the extract.

However, what can be known from a functional composition using thistle in the related art is that there is a substance which binds to an estrogen receptor in thistle, but it is impossible to know what kind of efficacy the thistle extract exhibits. Moreover, a phytoestrogen such as genistein, daidzein, or quercetin detected from the Korean native thistle is highly likely to bind to an estrogen receptor due to the structural similarity thereof, but as explained above, an actual effect caused by the binding has not been specifically revealed, and it is known that the ratio of binding is also at an insignificant level. Furthermore, since phytoestrogen is known to be present in most of the plants, the thistle composition described in Korean Patent Application No. 10-2009-0062458 has no new meaning.

Recently, as a phenomenon in which the concentration of estrogen is reduced has been recognized as a disease in addition to secondary symptoms such as facial flushing caused by a decrease in concentration of estrogen in the human body, numerous studies have been conducted for the purpose of directly treating the disease, and as described above, the disease in which the concentration of estrogen in a woman's body is reduced refers to estrogen deficiency (hypoestrogenism). Further, since hypogonadism means that the function of the ovary deteriorates, and as a result, sex hormones are reduced, it can be said that hypogonadism is included within a category of hypoestrogenism.

Accordingly, there is a need for research and development into a natural substance which fundamentally can prevent or improve estrogen deficiency and minimizes side effects, and the present inventors confirmed that a thistle extract and a thistle and thyme complex extract increase estrogen in a climacteric woman's body, thereby completing the present invention.

Thistle (*Cirsium japonicum*) is a perennial grass of the family Asteraceae, the order Campanulales, and the class Magnoliopsida, also refers to spiny herbs, and mainly grows in mountains or fields. Young shoots are used for edible purpose, and leaves, stems, and roots are used for medicinal purpose.

Thyme (*Thymus vulgaris*) is a semi-deciduous shrub of the family Lamiaceae, the order Tubiflorales, and the class Magnoliopsida, and examples thereof include the family thistle growing in high mountains in various places of Korea, *Thymus quinquecostatus* var. *japonica* growing in rocky places by the shore lines, *Thymus quinquecostatus* for. *albus* with white flowers in bloom, and the like. The thyme is used as a beverage, a disinfectant, a raw material for cosmetics, or a medicine.

Meanwhile, the constitution capable of improving estrogen deficiency by using the thistle extract and the thistle and thyme complex extract of the present invention may appear to be similar to Korean Patent Application No. 10-2009-0062458, but the constitution in which the thistle extract is effective for estrogen deficiency is not a matter which can be derived from the fact that phytoestrogen is present in thistle in Korean Patent Application No. 10-2009-0062458, and an existing study result made public also stated that phytoestrogen has nothing to do with the adjustment of female hormones in the human body {Cheng, et al. (2007) Isoflavone Treatment for Acute Menopausal symptoms. Menopause, 14, pp 468-473}.

DISCLOSURE

Technical Problem

An object of the present invention is to provide a functional composition for prevention and improvement of estrogen deficiency, the composition capable of effectively preventing and improving a symptom in which estrogen in climacteric women is reduced and efficiently alleviating symptoms occurring in relation to the women climacteric period and the composition using thistle which is composed of natural ingredients and thus can reduce a rejection response to a human body.

Technical Solution

A technical solution of the present invention is to provide a food composition for prevention and improvement of estrogen deficiency, the composition containing a thistle extract as an active ingredient.

Further, a technical solution of the present invention is to provide a food composition for prevention and improvement of estrogen deficiency, the composition containing a thistle and thyme complex extract as an active ingredient.

Advantageous Effects

The thistle extract and the thistle and thyme complex extract according to the present invention may alleviate estrogen deficiency which is a symptom in which estrogen in climacteric women is reduced.

Further, it is possible to further efficiently improve symptoms caused by estrogen deficiency, such as facial flushing, sweating, fatigue, anxiety, depression, memory impairment, insomnia, increased blood cholesterol, weight gain, and reduced bone density by directly increasing the concentration of estrogen in a climacteric woman's body.

DESCRIPTION OF DRAWINGS

FIGS. 1 to 8 are graphs illustrating results of measuring the concentration of blood estradiol in test animals.

FIG. 9 is a graph illustrating weight gain in test animals.

FIG. 10 is a graph illustrating a change in weight of test animals.

FIG. 11 is a graph illustrating an increment in blood alkaline phosphatase of test animals.

FIG. 12 is a graph illustrating an increment in blood osteocalcin of test animals.

FIG. 13 is a graph illustrating the improvement ratios of climacteric symptoms of test women, measured by a KI assay.

FIG. 14 is a graph illustrating MRS scores of test women, measured by an MRS assay.

BEST MODE

Figure 1:
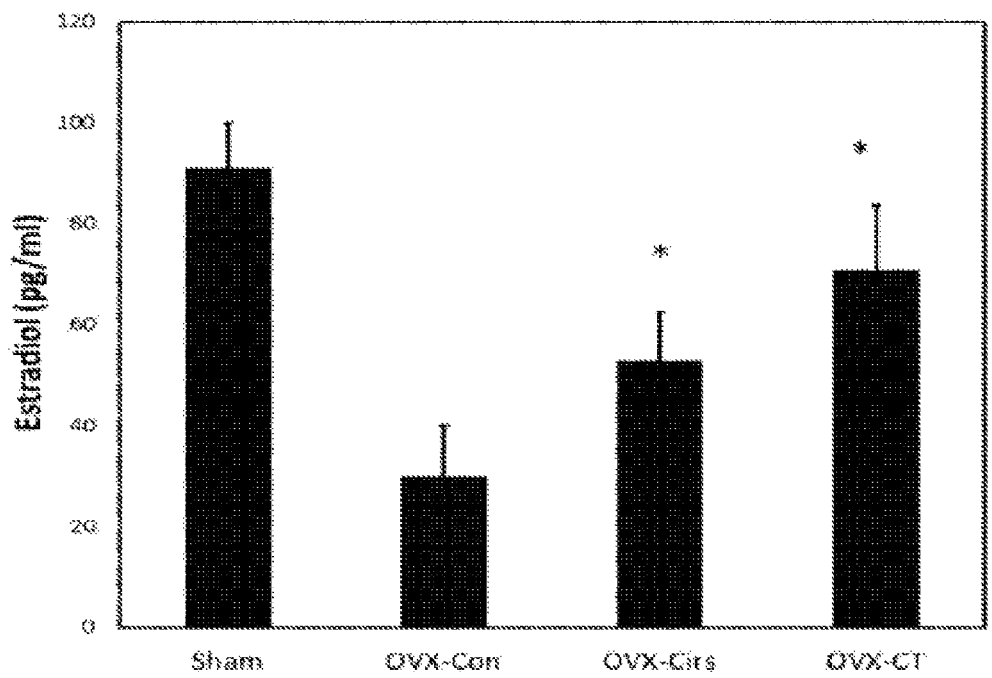

Before the present invention is described, the meaning of the terms used in the present invention will be described.

In the present specification, the term 'extract' has a meaning commonly used as a crude extract in the art, but also includes a meaning of a fractionated product obtained by additionally fractionating the extract in a wide sense. That is, a thistle extract includes not only those obtained by using the above-described extraction solvent, but also those obtained by additionally applying a purification process. For example, a fraction obtained by allowing the extract to pass through an ultrafiltration membrane having a predetermined molecular weight cut-off value, and a fraction obtained through various purification methods such as separation by means of various chromatography methods (those manufactured for separation according to the size, charge, and hydrophobicity or hydrophilicity) additionally carried out are included in the thistle complex extract of the present invention.

In the present specification, 'containing as an active ingredient' means including an amount of a thistle extract sufficient to achieve the efficacy or activity. The present invention is a composition extracted from thistle which is a natural plant material, and has no side effects on the human body even though the composition is administered in excess, and accordingly, the upper limit of the amount of thistle extract included in the composition of the present invention may be selected within an appropriate range and carried out by a person skilled in the art.

Hereinafter, the composition of the present invention will be described in detail.

The thistle extract according to the present invention is extracted by using an organic solvent, and those which may be used as an extraction solvent are as follows.

First, examples of those suitable as a polar solvent include (i) water, (ii) alcohol having 1 to 6 carbon atoms (preferably, methanol, ethanol, propanol, butanol, normal-propanol, iso-propanol, normal-butanol, 1-pentanol, 2-butoxyethanol or ethylene glycol), (iii) acetic acid, (iv) dimethyl-formamide (DMFO), and (v) dimethyl sulfoxide (DMSO), and the like.

Moreover, examples of those suitable as a non-polar solvent include acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride, methylene chloride, petroleum ether, THF, and the like.

It is preferred that the present invention uses (a) water, (b) an anhydrous or lower alcohol having 1 to 4 carbon atoms (methanol, ethanol, propanol, butanol, and the like), (c) a mixed solvent of the lower alcohol and water, (d) acetone, (e) ethyl acetate, (f) chloroform, (g) butyl acetate, (h) 1,3-butyelene glycol, (i) hexane, (j) diethyl ether, and the like as the extraction solvent, and it is more preferred that for facilitated extraction, the extraction is carried out by treating thistle with water, ethanol, or a mixture of water and ethanol.

Further, the thistle extract used in the present invention may be prepared in a powder state by an additional process such as distillation under reduced pressure and lyophilization or spray drying.

Therefore, the present invention may prepare an extract by using the aforementioned extraction solvent, and a method for preparing a thistle extract will be described below.

1) Preparation of Thistle Extract

①Thistle is sorted and ground, and ② then an extraction is carried out repeatedly by using a solvent selected from water including purified water with a volume amount (v/w<¾) which is about 1 to 25 times, preferably 7 to 15 times the weight of the ground substance, a lower alcohol having 1 to 4 carbon atoms, such as methanol, ethanol, and butanol, or a mixed solvent thereof, more preferably water, ethanol, or a mixed solvent thereof, ③ at an extraction temperature of 0 to 120° C., preferably 50 to 100° C., ④ for about 1 hour to 10 days, preferably about 3 hours to 6 hours ⑤ by means of an extraction method such as cold brew extraction, hot water extraction, ultrasonic extraction, reflux cooling extraction, or heated extraction, preferably hot water extraction or reflux cooling extraction, and ⑥ about one time to ten times, preferably two times to eight times. Moreover, a thistle extract is obtained by ⑦ filtering the extract by a filter cloth, ⑧ concentrating the filtrate under vacuum, and then ⑨-① lyophilizing the filtrate or ⑨-② mixing the concentrate with dextrin according to the blending ratio and spray drying the resulting mixture.

Further, the thistle extract may be prepared through a subcritical extraction method which extracts the extract by using a subcritical fluid, or a supercritical extraction method which extracts the extract by using a supercritical fluid.

As a thistle extract used in a test to be described below, an extract prepared by using a hot water extraction and an organic solvent extraction (ethanol, methanol) is used, and each extraction condition is as follows.

Thistle Extract 1 is prepared by carrying out a primary extraction at 121° C. for 5 hours using purified water with a volume amount which is 7 times the weight of the ground substance, carrying out a secondary extraction by adding purified water with a volume amount which is 5 times the weight of the ground substance thereto, concentrating the resulting extract under vacuum, and then mixing the extract and dextrin at 1:1, and spray drying the resulting mixture.

Thistle Extract 2 is prepared by carrying out a primary extraction at 100° C. for 5 hours using purified water with a volume amount which is 7 times the weight of the ground substance, carrying out a secondary extraction by adding purified water with a volume amount which is 5 times the weight of the ground substance thereto, concentrating the resulting extract under vacuum, and then mixing the extract and dextrin at 1:1, and spray drying the resulting mixture.

Thistle Extract 3 is prepared by carrying out a primary extraction at 70° C. for 5 hours using purified water with a volume amount which is 7 times the weight of the ground substance, carrying out a secondary extraction by adding purified water with a volume amount which is 5 times the weight of the ground substance thereto, concentrating the resulting extract under vacuum, and then mixing the extract and dextrin at 1:1, and spray drying the resulting mixture.

Thistle Extract 4 is prepared by carrying out a primary extraction at 70° C. for 5 hours using 40% ethanol with a volume amount which is 7 times the weight of the ground substance, carrying out a secondary extraction by adding 40% ethanol with a volume amount which is 5 times the weight of the ground substance thereto, concentrating the resulting extract under vacuum, and then mixing the extract and dextrin at 1:1, and spray drying the resulting mixture.

Thistle Extract 5 is prepared by carrying out a primary extraction at 50° C. for 5 hours using 90% ethanol with a volume amount which is 7 times the weight of the ground substance, carrying out a secondary extraction by adding 90% ethanol with a volume amount which is 5 times the weight of the ground substance thereto, concentrating the resulting extract under vacuum, and then mixing the extract and dextrin at 1:1, and spray drying the resulting mixture.

Thistle Extract 6 is prepared by carrying out a primary extraction at 70° C. for 5 hours using 40% methanol with a volume amount which is 7 times the weight of the ground substance, carrying out a secondary extraction by adding 40% methanol with a volume amount which is 5 times the weight of the ground substance thereto, concentrating the resulting extract under vacuum, and then mixing the extract and dextrin at 1:1, and spray drying the resulting mixture.

Thistle Extract 7 is prepared by carrying out a primary extraction at 50° C. for 5 hours using 90% methanol with a volume amount which is 7 times the weight of the ground substance, carrying out a secondary extraction by adding 90% methanol with a volume amount which is 5 times the weight of the ground substance thereto, concentrating the resulting extract under vacuum, and then mixing the extract and dextrin at 1:1, and spray drying the resulting mixture.

2) Preparation of Thyme Extract

A thyme extract is also prepared by the same preparation method as the thistle extract.

As a thyme extract used in a test to be described below, an extract prepared by using a hot water extraction and an organic solvent extraction (ethanol, methanol) is used, and each extraction condition is as follows.

Thyme Extract 1 is prepared by carrying out a primary extraction at 121° C. for 6 hours using purified water with a volume amount which is 6 times the weight of the ground substance, carrying out a secondary extraction by adding purified water with a volume amount which is 6 times the weight of the ground substance thereto, concentrating the resulting extract under vacuum, and then mixing the extract and dextrin at 1:1, and spray drying the resulting mixture.

Thyme Extract 2 is prepared by carrying out a primary extraction at 100° C. for 6 hours using purified water with a volume amount which is 6 times the weight of the ground substance, carrying out a secondary extraction by adding purified water with a volume amount which is 6 times the weight of the ground substance thereto, concentrating the resulting extract under vacuum, and then mixing the extract and dextrin at 1:1, and spray drying the resulting mixture.

Thyme Extract 3 is prepared by carrying out a primary extraction at 70° C. for 6 hours using purified water with a volume amount which is 6 times the weight of the ground substance, carrying out a secondary extraction by adding purified water with a volume amount which is 6 times the weight of the ground substance thereto, concentrating the resulting extract under vacuum, and then mixing the extract and dextrin at 1:1, and spray drying the resulting mixture.

Thistle Extract 4 is prepared by carrying out a primary extraction at 70° C. for 6 hours using 40% ethanol with a volume amount which is 6 times the weight of the ground substance, carrying out a secondary extraction by adding 40% ethanol with a volume amount which is 6 times the weight of the ground substance thereto, concentrating the resulting extract under vacuum, and then mixing the extract and dextrin at 1:1, and spray drying the resulting mixture.

Thistle Extract 5 is prepared by carrying out a primary extraction at 50° C. for 6 hours using 90% ethanol with a volume amount which is 6 times the weight of the ground substance, carrying out a secondary extraction by adding 90% ethanol with a volume amount which is 6 times the weight of the ground substance thereto, concentrating the resulting extract under vacuum, and then mixing the extract and dextrin at 1:1, and spray drying the resulting mixture.

Thistle Extract 6 is prepared by carrying out a primary extraction at 70° C. for 6 hours using 40% methanol with a volume amount which is 6 times the weight of the ground substance, carrying out a secondary extraction by adding 40% methanol with a volume amount which is 6 times the weight of the ground substance thereto, concentrating the resulting extract under vacuum, and then mixing the extract and dextrin at 1:1, and spray drying the resulting mixture.

Thistle Extract 7 is prepared by carrying out a primary extraction at 50° C. for 6 hours using 90% methanol with a volume amount which is 6 times the weight of the ground substance, carrying out a secondary extraction by adding 90% methanol with a volume amount which is 6 times the weight of the ground substance thereto, concentrating the resulting extract under vacuum, and then mixing the extract and dextrin at 1:1, and spray drying the resulting mixture.

3) Preparation of Thistle and Thyme Complex Extract

A thistle extract and a thyme extract which correspond to each condition are mixed at a ratio of 6:4. For example, Thistle and Thyme Complex Extract 1 is prepared by mixing Thistle Extract 1 and Thyme Extract 1, Thistle and Thyme Complex Extract 2 is prepared by mixing Thistle Extract 2 and Thyme Extract 2, and in this manner, Thistle and Thyme Complex Extracts 3 to 7 are prepared. And extracts, in which Thistle Extract 1 and Thyme Extract 1 are mixed at a ratio of 2:8, 4:6, and 8:2, are additionally prepared.

The thistle extract according to the present invention is prepared as a food composition. That is, the thistle extract according to the present invention may be prepared as a food composition for prevention and improvement of estrogen deficiency, the composition containing a thistle extract as an active ingredient.

When the thistle extract according to the present invention is prepared as a food composition, the thistle extract contains an ingredient typically added when a food is prepared, and for example, protein, carbohydrate, fat, a nutrient, and a seasoning agent correspond to the ingredient. Furthermore, when the thistle extract according to the present invention is prepared as a drink preparation, the thistle extract may contain a flavoring agent, natural carbohydrate, and the like as an additional ingredient in addition to the thistle extract as an active ingredient. For example, the natural carbohydrate includes monosaccharides (glucose, fructose, and the like), disaccharides (maltose, sucrose, and the like), oligosaccharides, polysaccharides (dextrin, cyclodextrin, and the like), and sugar alcohols (xylitol, sorbitol, erythritol, and the like). As the flavoring agent, it is possible to use natural flavoring agents (for example, thaumatin, stevia extract, and the like) and synthetic flavoring agents (for example, saccharin, aspartame, and the like).

Meanwhile, even when a thistle and thyme complex extract is prepared as a food composition, the preparation method thereof is the same as those described above. The effects of the thistle extract according to the present invention will be described in detail below by way of Test Examples.

TEST EXAMPLE 1

Animal Test

<1-1> Test Subject

After 7-week-old female rats having a body weight of 200 to 250 g were acclimated in a laboratory for 1 week, a menopausal model was induced by performing an ovariectomy on some of the female rats, and a non-menopausal model was induced by performing a sham-operation that cuts open the abdomen and then sutures the abdomen on the other female rats. Furthermore, after each model was fed with a solid feed for 1 week and recovered from the wound, five female rats were assigned to a control in which the ovary was not excised (hereinafter, referred to as 'a normal control') and five female rats were assigned to a control in which the ovary was excised (hereinafter, referred to as 'a negative control'), 30 female rats were assigned to a first experimental group (hereinafter, referred to as 'a first experimental group') in which the ovary was excised, and 21 female rats were assigned to a second experimental group (hereinafter, referred to as 'a second experimental group') in which the ovary was excised.

The first experimental group was divided into 7 groups of 3 female rats per group, and Thistle Extracts 1 to 7 dissolved at a concentration of 50 mg/kg in physiological saline were orally administered to each group. After the second experimental group was divided into 10 groups of 3 female rats per group, Thistle and Thyme Complex Extracts 1 to 7 dissolved at a concentration of 50 mg/kg in physiological saline were orally administered to 7 groups, thistle and thyme complex extracts in which Thistle Extract 1 and Thyme Extract 1 were mixed at a ratio of 2:8, 4:6, and 8:2 were orally administered to the other 3 groups, and the same amount of physiological saline was orally administered to the normal control and the negative control. For reference, the administration period was 8 weeks, the breeding conditions were a temperature of 24±2° C. and a humidity of 50 to 55%, and water and diet were provided without restriction.

<1-2> Measurement of Estrogen in Body

A reduction of estrogen is a representative cause of the occurrence of women climacteric symptoms. Accordingly, in the present invention, the concentration of blood estradiol-17β after the administration of a drug was measured in order to confirm effects of the thistle extract on estrogen. For reference, estradiol is a representative estrogen, and is used as an estrogen measurement subject due to the very high activity compared to estron or estriol.

Figure 2:
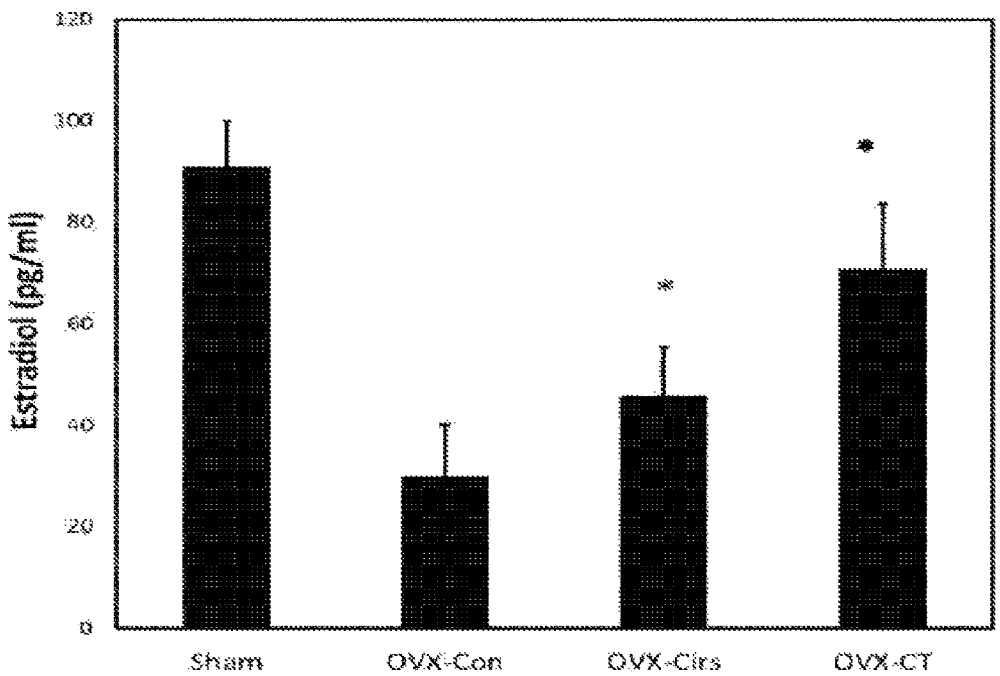
Figure 3:
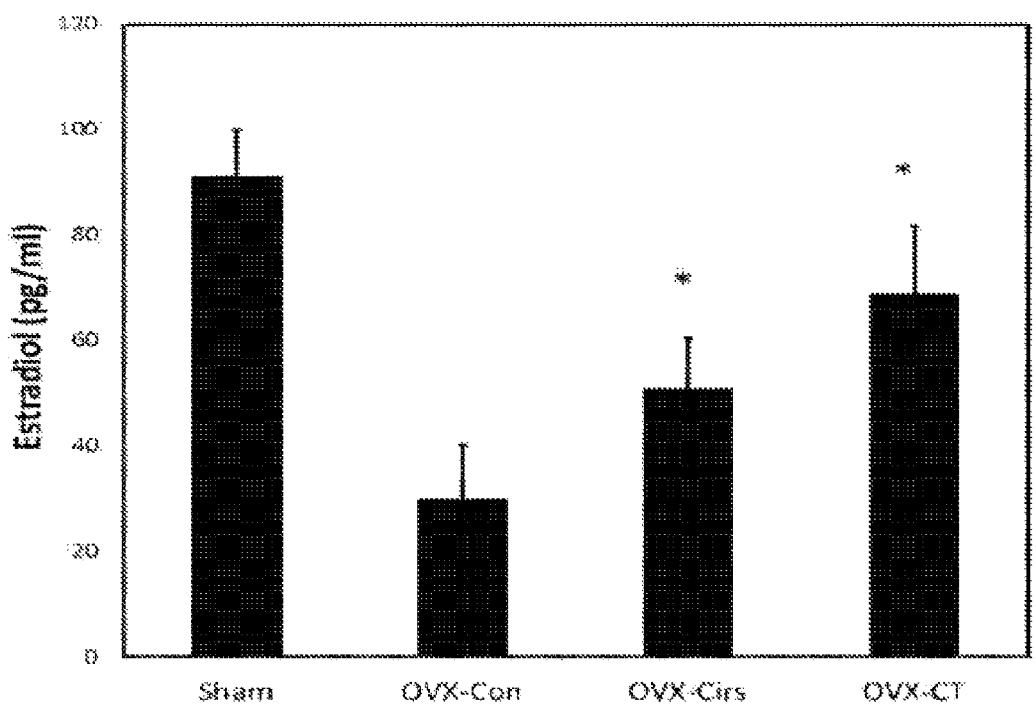
Figure 3:
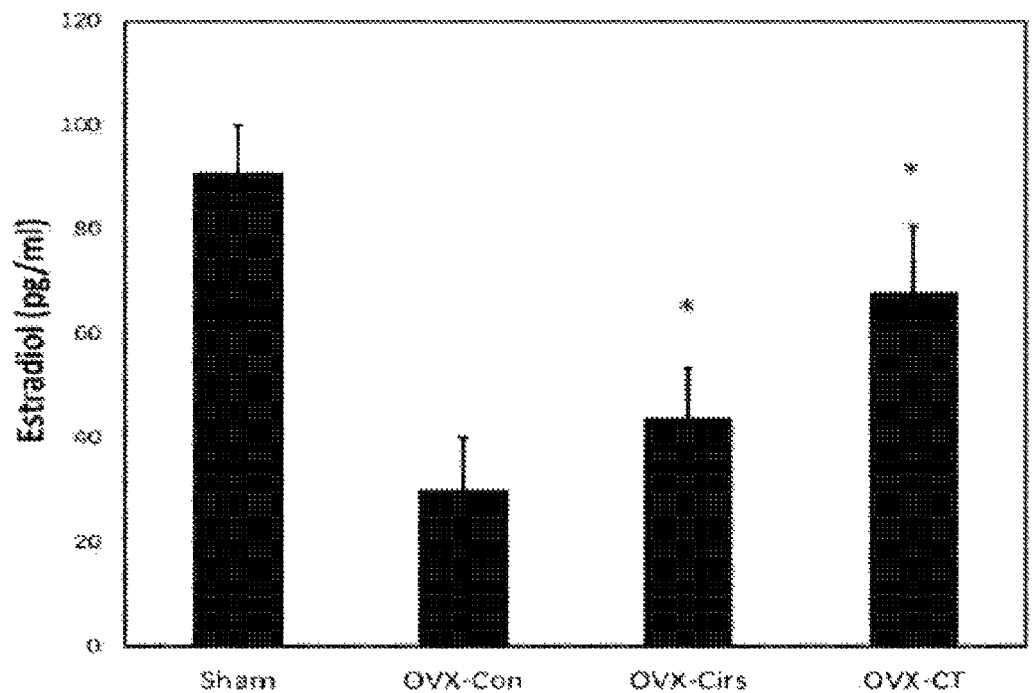

Specifically, blood was collected from each group in which the rats in <1-1> Test Subject were completely administered, was centrifuged (1,000 g, 15 min, 4° C.), and stored at −80° C. in a deep freezer prior to an analysis. Furthermore, blood estradiol was measured by using Rat estradiol (E2) ELISAKit (Cayman, Ann Arbor, Mich., USA). The significance was verified at a level of $p<0.05$ by a statistical treatment of the test result through a statistical program SPSS (version 12.0), and the result of measuring blood estradiol for each extract is illustrated in FIGS. 1 to 8. That is, the results according to Thistle Extract 1 and Thistle and Thyme Complex Extract 1 are illustrated in FIG. 1, the results according to Thistle Extract 2 and Thistle and Thyme Complex Extract 2 are illustrated in FIG. 2, the results according to Thistle Extract 3 and Thistle and Thyme Complex Extract 3 are illustrated in FIG. 3, the results according to Thistle Extract 4 and Thistle and Thyme Complex Extract 4 are illustrated in FIG. 4, the results according to Thistle Extract 5 and Thistle and Thyme Complex Extract 5 are illustrated in FIG. 5, the results according to Thistle Extract 6 and Thistle and Thyme Complex Extract 6 are illustrated in FIG. 6, the results according to Thistle Extract 7 and Thistle and Thyme Complex Extract 7 are illustrated in FIG. 7, and the results according to the mixture ratio of Thistle Extract 1 and Thyme Extract 1 are illustrated in FIG. 8.

For reference, the results of the normal control (Sham) and the negative control (OVX-Con) are each included in FIGS. 1 to 7 for a smooth comparison.

Judging from the fact that the concentration of blood estradiol in the negative control (OVX-Con) is significantly lower than that in the normal control (Sham) as illustrated in FIG. 1, it can be seen that the activity of estrogen is reduced due to the menopause. In addition, judging from the fact that the concentration of blood estradiol in the first experimental group (OVX-Cirs) was shown to be higher than that in the negative control (OVX-Con), it can be seen that the thistle extract is effective for alleviating a sharp drop in concentration of estrogen after menopause. Furthermore, judging from the fact that the concentration of estradiol in the second experimental group (OVX-CT) was measured to be higher than that in the first experimental group (OVX-Cirs), it can be seen that the thistle and thyme complex extract is more effective for an increase in concentration of blood estrogen.

Judging from the fact that FIGS. 2 to 7 also had a slight difference from FIG. 1, and exhibited the results in a similar pattern as FIG. 1, it can be seen that the efficacies of the thistle extracts and the thistle and thyme complex extracts are not significantly affected by the extraction solvent or the temperature.

Furthermore, FIG. 8 is a result of measuring the concentration of estradiol according to the mixture ratio of Thistle Extract 1 and Thyme Extract 1, and it can be seen that when a mixture, in which Thistle Extract 1 and Thyme Extract 1 were mixed at a ratio of 8:2, was administered to the test subjects, the highest concentration of estradiol was measured.

<1-3> Measurement of Body Weight

Weight gain is one of the representative symptoms in women during the climacteric period. Accordingly, in the present invention, a change in body weight according to the administration period was measured in order to confirm effects of the thistle extract on the body weight.

Specifically, the body weights of each group {in the case of the first experimental group, a group to which Thistle Extract 1 was administered and in the case of the second experimental group, a group to which Thistle and Thyme Complex Extract 1 (at a ratio of 6:4) was administered} were measured for a total of 9 weeks from the period when the drug was administered for 8 weeks prior to the administration of the drug until the period of 1 week after the administration of the drug. The significance was verified at a level of p<0.05 compared to the normal control by a statistical treatment of the test result through a statistical program SPSS (version 12.0), and the result thereof is illustrated in FIGS. 9 and 10.

Judging from the fact that the body weight in the negative control (OVX-Con) is significantly increased compared to that in the normal control (Sham) as illustrated in FIG. 9, it can be seen that the menopause affects an increase in body weight to some degree. Furthermore, it can be seen that an increase in body weight in the first experimental group (OVX-Cirs) was relatively less than that in the negative control (OVX-Con). Further, as illustrated in FIG. 10, it can be seen that after 9 weeks, the first experimental group (OVX-Cirs) made no big difference in the increase in body weight as compared to the normal control (Sham). Accordingly, it can be seen that the thistle extract is effective for alleviating an increase in body weight after the menopause.

Meanwhile, judging from the fact that the body weight in the second experimental group (OVX-CT) was increased at a lower ratio than that in the first experimental group (OVX-Cirs), it can be seen that the thistle and thyme complex extract more effectively acts in an increment in body weight in the climacteric period.

<1-4> Measurement of Cholesterol in Body

Healthy young women have lower blood total cholesterol, LDL-cholesterol, and triglyceride levels and a higher HDL-cholesterol level than those of men at the same age. However, when the menopausal period comes, it is known that the triglyceride and HDL-cholesterol levels are not usually changed, but the total cholesterol and LDL-cholesterol levels are increased, and these changes increase the incidence rate of vascular diseases after the women's menopausal period. Accordingly, in the present invention, the concentration of blood cholesterol after administration of a drug was measured in order to confirm effects of the thistle extract and the thistle and thyme complex extract on blood cholesterol.

Specifically, blood was collected from each group in which the administration was completed in <1-1> Test Subject { in the case of the first experimental group, a group to which Thistle Extract 1 was administered and in the case of the second experimental group, a group to which Thistle and Thyme Complex Extract 1 (at a ratio of 6:4) was administered}. Furthermore, sera were separated, and the concentrations of triglyceride, total cholesterol, and HDL-cholesterol in the serum were measured at a wavelength of 400 to 600 nm by Dry Chemistry Analyzer 3500i (Fuji, Japan) using a slide for automatic measurement (Fuji Film, Japan). In the case of HDL-cholesterol, the HDL-cholesterol level in the supernatant was measured by precipitating chylomicron, low-density lipoprotein and very low density lipoprotein with a precipitating agent. The LDL-cholesterol level was calculated by the following Friedewald equation.

LDL Cholesterol Level={Total Cholesterol Level−
(HDL-Cholesterol Level−Triglyceride Level/5)}

The study results were expressed as mean±standard deviation, the significance was verified at a level of p<0.05 by a statistical treatment of the study result through a statistical program SPSS (version 12.0), and the results are shown in Table 1.

TABLE 1

| Classification | Total cholesterol level | Triglyceride level | HDL-cholesterol level | LDL-cholesterol level |
|---|---|---|---|---|
| Normal control | 84.86 ± 5.67* | 63.92 ± 4.59* | 50.80 ± 5.64* | 46.84 ± 5.75* |
| Negative control | 117.36 ± 8.25 | 89.80 ± 8.93 | 40.60 ± 4.18 | 94.72 ± 13.28 |
| First experimental group | 94.80 ± 4.44* | 71.24 ± 4.15* | 48.40 ± 4.18* | 60.65 ± 6.75* |
| Second experimental group | 89.92 ± 11.80* | 67.23 ± 3.61* | 49.60 ± 2.06* | 53.77 ± 11.39* |

(Unit: mg/dl)

As a result of the experiments, as in Table 1, blood total cholesterol, triglyceride, and LDL-cholesterol levels were significantly increased and the HDL-cholesterol level was decreased in the negative control as compared to those in the normal control. Conversely, in the first experimental group and the second experimental group, the blood total cholesterol, triglyceride, and LDL-cholesterol levels were significantly lower and the HDL-cholesterol level was higher than those in the negative control (OVX-Con).

Accordingly, through the result of the present test example, it can be seen that the thistle extract and the thistle and thyme complex extract, which are the compositions of the present invention, are effective for improving the blood lipid content, hyperlipidemia caused by the blood lipid content, and the like in a menopausal situation.

<1-5> Measurement of Bone Index

The reduced bone density is one of the symptoms occurring in climacteric women, and is responsible for causing diseases such as osteoporosis. Accordingly, in the present invention, the concentration of blood alkaline phosphatase (hereinafter, referred to as 'ALP') and the concentration of osteocalcin (hereinafter, referred to as 'OC') after administration of a drug were measured in order to confirm effects of the thistle extract and the thistle and thyme complex extract on bone density.

Specifically, blood was collected from each group in which the administration was completed in <1-1> Test Subject {in the case of the first experimental group, a group to which Thistle Extract 1 was administered and in the case of the second experimental group, a group to which Thistle and Thyme Complex Extract 1 (at a ratio of 6:4) was administered}. The concentration of blood ALP was analyzed by using an automatic analyzer (ADVIA 1650, Bayer, Tokyo, Japan), and the concentration of blood OC was analyzed by using ELISA kit (Metra OC, Quidel Corporation, San Diego, Calif., USA).

The significance was verified at a level of $p<0.05$ compared to the normal control by a statistical treatment of the test result through a statistical program SPSS (version 12.0), and the result thereof is illustrated in FIGS. 11 and 12. As a result of the experiments, as illustrated in FIGS. 11 and 12, the concentrations of blood ALP and OC in the negative control (OVXCon) were increased as compared to those in the normal control (Sham). The result described above can be considered as a procedure in which the bone reformation procedure is increased by reduced bone density caused by ovariectomy, and bone replacement indices are enhanced during the bone reformation procedure. Accordingly, during the procedure, the concentration of blood ALP, which is a representative bone replacement index, is increased, and the concentration of OC, which is a bone reabsorption and bone formation index, is increased (Hertrampf T., Schleipen B., Offermanns C., Velders M., Laudenbach U., Diel P., Comparison of The Bone Protective Effects of Anisoflavone-Rich Diet With Dietary and Subcutaneous Administrations of Genistein in Ovariectomized Rats. Toxicol. Lett. 2009, 184, 198-203.). In contrast, the concentrations of blood ALP and OC in the first experimental group (OVX-Cirs) were reduced as compared to those in the negative control (OVX-Con). Further, in the second experimental group (OVX-CT), the concentrations of blood ALP and OC were reduced than those in the first experimental group, so that a numerical value closest to the normal control (Sham) was produced.

Accordingly, judging from the fact that the concentrations of blood ALP and OC were relatively less increased, it can be seen that the thistle extract and the thistle and thyme complex extract are effective for alleviating a decrease in bone density caused by the menopause.

TEST EXAMPLE 2

Human Body Test

<2-1> Test Subject

Among 60 middle-aged women at the age of 45 years or older, who agreed to the present assay, 20 women were arbitrarily classified into a control (Placebo) in which a placebo was taken, a first experimental group (Cirs) in which a thistle extract was taken, and a second experimental group in which a thistle and thyme complex extract (CT) was taken per group, and were allowed to take 400 mg of a placebo or an experimental drug containing a thistle extract or a thistle and thyme complex extract daily for 12 weeks.

<2-2> Korean Version KI (Kupperman's Index)

This is an assay published by setting 11 representative symptoms in the climacteric period as items as in Table 2 based on clinical treatment experiences of climacteric disorders by Kupperman in 1953 and grasping the degree and characteristics of climacteric disorders, and is a self-questionnaire assay method which is most commonly used as a measure of evaluating the symptom among studies related to women climacteric symptoms up until now. The degree and characteristics of each symptom in the climacteric period are grasped, the products obtained by multiplying a score for each item were added up, and 20 points or less, 20 to 40 points, 40 to 60 points, and 60 points or more are determined as a mild symptom, an intermediate symptom, and a serious state, respectively. A result in which the improvement rate was calculated after the intake is illustrated in FIG. 13, and the significance was verified at a level of $p<0.05$ by a statistical treatment of the result through a statistical program SPSS (version 12.0).

TABLE 2

| Symptom | Not experienced at all | Sometimes experienced | Frequently experienced | Always experienced |
| --- | --- | --- | --- | --- |
| 1. Facial flushing | | | | |
| 2. Sweating | | | | |
| 3. Insomnia | | | | |
| 4. Nervousness | | | | |
| 5. Depression | | | | |
| 6. Vertigo | | | | |
| 7. Fatigue | | | | |
| 8. Arthralgia, Myalgia | | | | |
| 9. Headache | | | | |
| 10. Palpitation | | | | |
| 11. Colpoxerosis, Reduced secretions | | | | |

As illustrated in FIG. 13, the control (Placebo) in which the placebo was taken exhibited a symptom improvement rate after the intake for 3 months by 4.2%, whereas the first experimental group (Cirsium) reduced women climacteric symptoms by 30%, which were evaluated by KI, and thus significantly improved the climacteric symptoms as compared to the control (Placebo). Further, in the second experimental group (C+Thyme), it can be seen that the women climacteric symptoms were reduced by 45% or more.

Accordingly, through the present result, it was confirmed that the thistle extract and the thistle and thyme complex extract could effectively improve complicated women climacteric symptoms, such as facial flushing, sweating, insomnia, nervousness, depression, vertigo, fatigue, arthralgia and myalgia, palpitation, colpoxerosis, and reduced secretions.

<2-3> Korean Version Menopause Rating Scale (MRS)

The MRS assay is an assay method produced in 1996 by newly complementing a MENopause-specific Quality of Life Questionnaire (MENQOL) assay produced by complementing the Kuppermanindex by Hildich et al., in 1992. While the MRS has been cited globally in numerous studies, the reliability and validity thereof have been recognized. The MRS is composed of 11 items in total, such as physical symptoms, mental symptoms, and urogenital symptoms, and has advantages in that the number of items is small, and the procedure is simple and convenient. The MRS as described above evaluates symptoms from the criteria as in the following Table 3.

The total score is calculated, and from the total score, 0 to 4 points are in a good climacteric state, meaning a happy climacteric period, and 5 to 8 points are in a mild climacteric state, showing that care is required. 9 to 15 points are in a severe climacteric state, and diagnosis and treatment by experts are required because a patient with these points has a climacteric disorder. 16 points or higher are in a serious climacteric state, and are a numerical value showing that long-term plans and treatments are considerably required.

The result is illustrated in FIG. 14, and the significance was verified at a level of $p<0.05$ by statistically analyzing points before and after the intake by each experimental group through a statistical program SPSS (version 12.0).

As a result of the test, the control (Placebo) did not exhibit a statistically significant difference in the MRS score after the intake for 3 months, as illustrated in FIG. 14. In contrast, in the first experimental group (Cirsium), it was confirmed that after the intake for 3 months, the MRS score was decreased by approximately 30%, and thus, the women climacteric symptoms were significantly reduced. Further, judging from the fact that in the second experimental group (C+Thyme), the results after the intake for 3 months exhibited a greater difference than those in the first experimental group, and the symptoms were reduced, it can be seen that it is possible to more effectively improve climacteric symptoms.

INDUSTRIAL APPLICABILITY

The thistle extract and the thistle and thyme complex extract according to the present invention may alleviate estrogen deficiency which is a symptom in which estrogen in climacteric women is reduced, and thus may be provided as an associated functional food or medicine, and the like.

The invention claimed is:

1. A composition which is effective for improving the blood lipid content in a human, improving hyperlipidemia in a human caused by the blood lipid content in a human, and improving estrogen deficiency in a human consisting essentially of dextrin, thistle extract, thyme extract and a solvent selected from the group consisting of acetone, ether, ben-

TABLE 3

| | State | | | | |
| --- | --- | --- | --- | --- | --- |
| Symptom | None (0) | Slight (1) | Fair (2) | Severe (3) | Very severe (4) |
| Facial flushing and sweating (an experience in which the face feels flushed or feverish and an experience in which sweat suddenly appears) | | | | | |
| Heart discomfort (suddenly palpitates and the pulse becomes fast or skips) | | | | | |
| Sleep problem (difficult to sleep or readily awake from sleep and difficult to continue sleep) | | | | | |
| Depressed mood (feeling despondent, sadness, readily shed tears, and no motivation) | | | | | |
| Hypersensitivity (feeling in which nerves become sharp, aggressive feeling, and tension) | | | | | |
| Anxiety (inner irritation and feeling of panic) | | | | | |
| Physical and mental fatigue (fatigue, lethargy, memory loss, reduced concentration, and forgetfulness) | | | | | |
| Sexual problems (sexual desire changes, changes in sexual behavior, and changes in sexual gratification) | | | | | |
| Urination problems (difficult to urinate, frequently urinate, and incontinence) | | | | | |
| Vaginal dryness (dryness or burning of vaginal areas, discomfort during sexual intercourse) | | | | | |
| Joint and muscle discomfort (joint pain, symptoms similar to rheumatism) | | | | | |
| Total score | | | | | | zene, chloroform, ethyl acetate, methylene chloride, hexane, cyclohexane and petroleum ether.

* * * * *